United States Patent [19]

Pariseau et al.

[11] Patent Number: 5,242,726
[45] Date of Patent: Sep. 7, 1993

[54] PATTERN-COATED ANCHORAGE SYSTEM FOR POROUS FILM

[75] Inventors: Timothy P. Pariseau, White Bear Lake; Terry L. Morris, Eagan, both of Minn.

[73] Assignee: Minnesota Mining and Manufacturing Company, St. Paul, Minn.

[21] Appl. No.: 763,675

[22] Filed: Sep. 23, 1991

[51] Int. Cl.$^5$ .............................................. C09J 7/00
[52] U.S. Cl. ................................. 428/40; 428/315.5; 428/317.7; 428/352
[58] Field of Search ............... 428/352, 355, 315.5, 428/317.7, 318.4, 40

[56] References Cited

U.S. PATENT DOCUMENTS

| | | | |
|---|---|---|---|
| Re. 24,906 | 12/1960 | Ulrich | 428/480 |
| 3,066,043 | 11/1962 | Hechtman | 428/355 X |
| 3,262,827 | 7/1966 | Kallander et al. | 156/230 |
| 3,441,430 | 4/1969 | Peterson | 428/354 |
| 3,643,662 | 2/1972 | McGuire et al. | 604/387 |
| 3,674,595 | 7/1972 | Reeder | 156/306 |
| 3,753,944 | 8/1973 | Sirota et al. | 524/500 |
| 3,865,770 | 2/1975 | Blake | 156/327 |
| 3,888,255 | 6/1975 | Shah et al. | 604/369 |
| 3,891,584 | 6/1975 | Ray-Chaudhuri et al. | 524/270 |
| 3,971,865 | 7/1976 | Murakami et al. | 428/40 |
| 4,136,699 | 1/1979 | Collins et al. | 428/40 |
| 4,272,573 | 6/1981 | Ewald et al. | 428/40 |
| 4,339,485 | 7/1982 | Shibano et al. | 428/40 |
| 4,391,853 | 7/1983 | Pointon | 427/152 |
| 4,413,080 | 11/1983 | Blake | 524/187 |
| 4,460,364 | 7/1984 | Chen et al. | 604/387 |
| 4,539,256 | 9/1985 | Shipman | 428/315.5 |
| 4,569,960 | 2/1986 | Blake | 524/145 |
| 4,704,110 | 11/1987 | Raykovitz et al. | 604/366 |
| 4,726,989 | 2/1988 | Mrozinski | 428/315.5 |
| 4,824,718 | 4/1989 | Hwang | 428/284 |
| 4,859,512 | 8/1989 | Jones et al. | 428/40 |
| 4,959,008 | 9/1990 | Wasulko | 428/40 |

FOREIGN PATENT DOCUMENTS

| | | |
|---|---|---|
| 0428017A2 | 5/1991 | European Pat. Off. |
| 1377575 | 12/1974 | United Kingdom . |
| 1420743 | 1/1976 | United Kingdom . |

Primary Examiner—George F. Lesmes
Assistant Examiner—Chrristopher Brown
Attorney, Agent, or Firm—Gary L. Griswold; Roger R. Tamte; William J. Bond

[57] ABSTRACT

An adhesive laminate structure composed of three layers is provided. A smooth thermoplastic film acts as a release liner without any release coating in combination with an acrylate adhesive and an oil-containing substrate.

14 Claims, No Drawings

PATTERN-COATED ANCHORAGE SYSTEM FOR POROUS FILM

BACKGROUND OF THE INVENTION

The present invention relates to a laminate structure of an oil-containing substrate having a transfer adhesive and an associated release liner thereon. Particularly, the invention relates to a laminate where the oil-containing substrate is a porous film.

Porous films are used in a wide array of garment and related-type applications such as surgical dressings, bandages, and feminine hygiene products. U.S. Pat. No. 4,824,718 discloses the use of a rattle-free liquid-impermeable, but vapor-permeable microporous sheet used on disposable articles such as diapers, adult incontinent products and feminine hygiene products. The microporous film disclosed is rendered rattle-free by use of an oily additive material such as mineral oil, glycerin, petroleum jelly, polyethylene, polyethylene oxide, polypropylene oxide, polytetramethylene oxide, soft carbowax, and the like, and mixtures thereof.

In the articles such as those disclosed in U.S. Pat. No. 4,824,718, frequently an adhesive patch is applied to the microporous film to enable the article having the microporous film to be attached to another article or another portion of itself. For example, U.S. Pat. No. 3,888,255 discloses a typical sanitary napkin construction where a strip of pressure-sensitive adhesive is supplied on the garment facing portion of the napkin for attachment to the crotch portion of the undergarment. The adhesive is protected when in not in use by peelable release liner, which generally would be a silicone-coated paper or silicone-coated polyolefin film. These release liners are removed when the adhesive is to be used and discarded. These release liners are problematic in that they are costly and difficult to manufacture.

U.K. Patent No. 1,377,575 discloses a sanitary napkin where the adhesive is transfer coated onto a nonwoven cover stock from a polyethylene film coated with a vinyl acrylate adhesive. However, it is required that the adhesive be applied to the nonwoven cover stock when it is still wet. As such, the adhesive must be applied to the polyethylene backing immediately prior to attachment to the sanitary napkin nonwoven material. Applying adhesive inline in this manner complicates production and production speed.

U.S. Pat. No. 4,136,699 describes a hot-melt pressure-sensitive adhesive specifically designed for use with sanitary napkins. The adhesive is designed for attaching these napkins to supporting undergarments. The adhesive disclosed is based on A—B—A block copolymer elastomers and is generally used in combination with a conventional release liner for protecting the adhesive layer prior to use. This liner would have a release coating such as a silicone. A problem with this type of adhesive is that it is not soluble in water and, if transferred to the undergarment, the adhesive is not easily washed off.

U.K. Patent Specification 1,420,743 describes a transfer tape product where the transfer film liner is coated with a silicone release material. This patent specification also mentions the possibility of using plastic films having inherently low degrees of affinity for adhesives such as a polyethylene. However, such films are rarely, if ever, used as they do not provide the premium release values obtained with the silicone and like release coated liners.

BRIEF SUMMARY OF THE INVENTION

A laminate is provided comprising an oil-containing substrate or base layer, an acrylate adhesive layer and a thermoplastic film. The thermoplastic film acts as a release liner in the laminate with peel release values of less than 100 g/in without a release coating. The oil-containing substrate is preferably an oil-containing microporous film, such as could be used in a feminine napkin or incontinent article, having at least 5% oil in the film matrix.

DETAILED DESCRIPTION OF THE PREFERRED EMBODIMENTS

The invention provides a laminate structure in which conventional thermoplastic films can be used as release liners and provide peel release values typically only obtainable with release-coated substrates, such as silicone coated release liners. The adhesive-coated thermoplastic film can be supplied as a transfer tape product and is attached to an oil-containing substrate such as a film to form the laminate. The adhesive is transferred to the oil-containing film, and the thermoplastic film protects the adhesive prior to use. Subsequently, the thermoplastic film liner can be removed at extremely low peel release values.

Suitable oil-containing films include those disclosed in U.S. Pat. Nos. 4,824,718, 4,726,989 and 4,539,256. These oil-containing films are produced from blends of crystallizable polymers with oils or oil-like liquids or solids which will dissolve, or are miscible with, the crystallizable polymer at a temperature around the polymer's melting point, but phase separate at lower temperatures to provide a film having a matrix of the crystallizable thermoplastic material with the phase separated material. These films were provided with adequate tensile properties by the crystallizable polymer matrix which is generally polyolefins such as polyethylenes, polypropylenes, polybutylenes, poly-4,methyl-1-pentenes, and copolymers and blends thereof. Generally, polypropylenes, or polyethylenes are preferred with polypropylenes being particularly preferred. The phase separable material is preferably those such as disclosed in U.S. Pat. No. 4,824,718 with mineral oil being preferred because of its low cost and its superior properties. Generally, this phase separable material is from 5 to 80 percent of the composition, preferably 5 to 50 percent, with the remaining portion of the composition substantially being the crystallizable polymer. Although not critical to the instant invention, these films can typically use a nucleating agent system, such as disclosed in U.S. Pat. Nos. 4,726,989 and 4,824,718, which generally is an admixture of a solid organic compound with an inorganic material. A preferred solid organic would be an organic acid miscible with the crystallizable polymer in its molten state, yet able to phase separate when the polymer is cooled. Examples of such solid organics include mono and poly acids such as carboxylic acids, sulfonic acids, phosphonic acids, solid organic alcohols and the like. The solid inorganic nucleating agent can be materials such as talc, titanium dioxide, calcium carbonate, magnesium carbonate, barium carbonate, magnesium sulfate, barium sulfate and the like. The particles are generally quite small with dimensions ranging in the micron-to-submicron range. Further, the inorganic nucleating agents are generally used at relatively low weight percents so as to minimize any effects on the film strength.

The composition is formed, typically extruded, into a film which is orientated uniaxially or biaxially at a temperature of about 10° C. below the melting point of the crystallizable matrix polymer. Generally, the stretch ratio is greater than 1.5 and can be as high as 12 or more.

If using a microporous film as described above, one can remove a portion of the oil-like, phase-separable additive by conventional processes, such as by use of a quench bath with a solvent capable of dissolving the oil or other additive compound, such as 1-1-1-trichloroethane for mineral oil. Sufficient oil must remain in the film to permit the thermoplastic film to function as a release liner in the invention laminate, generally at least 5% of the film, preferably at least 20%. Other suitable oil-containing substrates can be used, which may or may not be films depending upon the application.

Suitable adhesives include acrylate-based adhesives such as repulpable adhesives using acrylic acid esters of non-tertiary alkyl alcohols, which are preferably copolymerized with monomers having strong polar groups such as vinyl carboxylic acid monomers. The polar groups are then at least partially neutralized to a water-soluble form, and the polymer tackified with water-soluble tackifiers or plasticizers. A particularly preferred adhesive would include those such as disclosed in U.S. Pat. No. 3,865,770, which discloses a rubbery copolymer of alkyl acrylates derived from non-tertiary alkyl alcohols having 1 to 14 carbon atoms in its chain copolymerized with vinyl carboxylic acid monomers. The copolymer is partially neutralized with a secondary or tertiary alkanol amine containing 4 to 18 carbon atoms to make the rubbery copolymer water-dispersable. A suitable alkanol amine is diethanol amine. The rubbery copolymer is then mixed with a water-dispersable tack-promoting agent which can be used in amounts of up to four times the amount of the rubber. Suitable tackifiers include acid rosins and their derivatives, and polyoxyalkylene plasticizers. Other suitable acrylic acid ester water-dispersable adhesives are disclosed in U.S. Pat. No. 4,569,960, based on a copolymer of acrylic acid ester of a non-tertiary alkyl alcohol (60-85 weight percent) and a vinyl carboxylic acid (40-25 weight percent), which is plasticized with a phosphoric acid ester or an OH functional ethoxylated plasticizer, such as ethyoxylated aminopropylamine. The acidic moieties and the copolymer are neutralized with a base such as potassium or sodium hydroxide so as to form salts of a least a portion of the acidic moieties to render the copolymer water-dispersable.

The acrylate adhesive formulation is provided on a film liner, suitably a thermoplastic film such as a polyolefin or a polyester film. The film is smooth on the face carrying the adhesive such that it has a low Ra value preferably of less than about 40, more preferably less than about 20. The preferred polyolefin is polypropylene. The adhesive can be provided on the film liner by any conventional method, such as solvent coating. This adhesive-backed film liner can then be used as a transfer tape to form the invention laminate with the oil-containing substrate or film. A highly unusual feature of the invention laminate is that when the adhesive-coated film liner or transfer tape is laminated to the oil-containing substrate, the thermoplastic film liner performs like a premium release-coated liner having 180° peel release values of about 100 grams/inch or less, preferably less than 50 grams/inch. Typically, peel release values of this low level are obtainable only by providing a film liner with a release coating such as a silicone, or the like.

In a particularly preferred embodiment, an acrylate adhesive is a repulpable formulation employed in a laminate construction as part of a feminine napkin or like applications where the repulpable adhesive is used to adhere an article using an oil-containing film to a garment. These adhesives provide adhesion properties adequate to function as an anchoring system to garments with relatively low levels of adhesive transfer. Further, the adhesive transfer problem is rendered negligible by the water-dispersable nature of the repulpable adhesive, as the adhesive will be easily removed in subsequent washings. The oil-containing film in these applications would preferably be a microporous film.

Other suitable applications for the invention laminate include garments, bandages, diapers or incontinent articles and other uses for oil-containing (e.g., microporous) films, where an adhesive patch or area on the oil-containing film is desirable. The adhesive in these constructions can be a continuous layer or pattern coated intermittently. Intermittent coating permits enhanced breathability in the adhesive-coated area for microporous films. Suitable intermittent coatings could be spaced lines, dots or other patterns.

The following examples are currently contemplated preferred modes for carrying out the invention and should not be considered as limiting thereof unless otherwise indicated.

EXAMPLES

Examples 1-8

A repulpable adhesive was placed into a solution (ethyl acetate/isopropanol/methyl alcohol) at 30% solids. The adhesive (RD 1286, available from 3M Company, St. Paul, Minn.) was a butylacrylate/acrylic acid (75/25 with an inherent viscosity of 1.9 to 2.2) copolymer admixed with Foral TM AX (a wood rosin), N-methyl diethanolamine, Pycal TM 94 (a tetraethylene glycol phenyl ether), and Ethoduomeen T/25 (PEG-15 tallow aminopropylamine available from Armak Corp.) prepared in accordance with U.S. Pat. No. 3,865,770. The adhesive solution was coated onto a variety of liner films (about 2 mils thick) as indicated in Table 1 below. The adhesives were coated at a weight of 2.8 grains/24 in$^2$ (18 grams/cm$^2$) sample. The coated adhesive was then allowed to dry for 1 minute at room temperature followed by 10 minutes at 150° F. (65° C.). The tape was then laminated to an oil-filled (about 34% oil) porous film of polypropylene (1.5 mils, 0.0381 mm), prepared as described in U.S. Pat. No. 4,539,256 and 4,726,989. The oil was mineral oil (Amoco White oil E31). The film had a Gurley value of 250 sec/50 cc (measured in accordance with ASTM-D-726-58, method A). The lamination was at room temperature. The film liners were then tested for 180° peel release of the liner from the porous film at 4 hours, 24 hours and 168 hours using ASTM D903-49 at a crosshead speed of 12 inches/minute. The results are given in Table 1 below (in grams/inch width).

TABLE 1

| Example | Backing (Lining) | 4 hr. Peel | 24 hr. Peel | 168 hr. Peel |
|---|---|---|---|---|
| 1 | Norchem TM 5112[1] | 62 | 78 | 82 |
| 2 | Norchem TM 6180[2] | 52 | 72 | 72 |
| 3 | Norchem TM 6180[3] | 65 | 75 | 82 |
| 4 | Shell | 32 | 10 | 10 |

TABLE 1-continued

| Example | Backing (Lining) | 4 hr. Peel | 24 hr. Peel | 168 hr. Peel |
|---|---|---|---|---|
| 5 | 5A95[4] Shell 7C04N[5] | | 23 | 30 |
| 6 | Fina W756[6] | 20 | 80 | 10 |
| 7 | Fina W756[3] | 17 | 80 | 10 |
| 8 | Norchem TM 5112[3] | 65 | 71 | 73 |

[1]Polyethylene; density 0.948, MI = 14 g/10 min.
[2]Polyethylene; density 0.960, MI = 1.15 g/10 min.
[3]With 0.2% Zn (stearate)
[4]Polypropylene, MFR = 9.5 g/10 min, Ra = 9 adhesive-coated face.
[5]Polyethylene/polypropylene nucleated impact copolymer MFR = 35.0 g/10 min.
[6]Polyethylene/polypropylene impact copolymer, MI = 7 g/10 min., 3.5% ethylene, also sold as Fina 8573A.

For all the above laminate constructions, the liner readily released from the porous film, leaving the adhesive attached to the porous film. Superior results were obtained with the polypropylene containing polymer liners of Examples 4–7 compared to the polyethylene liners of Examples 1–3 and 8.

Examples 1–8 samples, without the liner, were then tested against cotton (basis weight 2.9 grams/24 in² with about 34 strands/inch) using the T-peel test at a rolldown pressure of 4.5 pounds. The 5 degree static shear from cotton was also tested for the adhesive-coated porous film samples of Examples 1–8. The results of this adhesion testing to cotton is set forth in Table 2 below.

TABLE 2

| Example | T-Peel (168 Hours) | 5° Shear | % Adhesive Transfer |
|---|---|---|---|
| 1 | 223 | 13 | 12 |
| 2 | 183 | 17 | 3 |
| 3 | 197 | 13 | 8 |
| 4 | 223 | 10 | 13 |
| 5 | 257 | 11 | 10 |
| 6 | 243 | 21 | 10 |
| 7 | 193 | 17 | 2 |
| 8 | 263 | 14 | 22 |

The T-peel values are given in grams/inch width and the shear in minutes. The adhesive transfer was determined visually after the T-Peel test. The peel values were generally high for all these examples with relatively small amounts of adhesive transfer. The nature of the liner generally did not appear to effect the nature of the subsequent adhesive performance to cotton.

Examples 9–17

Laminates were prepared as described above for Examples 1–8 except that the liner for all the example laminates was Shell 5A95, and the porous films (all oil-filled porous films contained about 34% oil) were varied as indicated in Table 3.

TABLE 3

| Example | Porous Film | 4 Hour Peel | 24 Hour Peel | 168 Hour Peel |
|---|---|---|---|---|
| C9 | Mitsui[1] | 108 | 147 | 143 |
| C10 | Kao[2] | 96 | 102 | 125 |
| 11 | Polypropylene[3] | 31 | 12 | 10 |
| C12 | Polypropylene[4] | 163 | 197 | 167 |
| 13 | Polypropylene[5] | 28 | 10 | 8 |
| 14 | Polypropylene[6] | 20 | 12 | 10 |
| C15 | Polyethylene[7] | 202 | 242 | 212 |
| C16 | Shell 5A95 Polypropylene | 285 | 83 | 87 |
| C17 | Norchem 5112 | | 113 | 103 |

C = counterexample.
[1]A particle-filled porous polyethylene film available from Mitsui-Toatsu, Gurley 800 sec/50 cc.
[2]A particle-filled porous polyethylene film available from KAO, Gurley 900 sec/50 cc.
[3]With mineral oil prepared as per U.S. Pat. No. 4,539,256 and 4,726,989, Gurley 250 sec/50 cc, stretched 1.6 × 1 (machine direction).
[4]The porous film of Example 3 with the oil washed out with toluene, Gurley 50 sec/50 cc.
[5]The porous film in accordance with Example 3, stretched 2.0 × 1 (machine direction), Gurley 95 sec/50 cc.
[6]The porous film in accordance with Example 3, stretched 1.2 × 1 (machine direction).
[7]With mineral oil washed out, prepared as per U.S. Pat. No. 4,539,256, stretched 2 × 2.

Examples 16 and 17 were non-porous, non-oil-containing films used for purposes of comparison. The 180° peel release values for the oil-filled porous films were extremely low providing premium release values for the liners used. The Examples 9 and 10 films are believed to have very low levels of plasticizing oils in their matrix.

Example 9–17 laminates, with the liners removed, were also evaluated with regard to their adhesion properties to cotton as described above for Examples 1–8. The results of this testing is set forth in Table 4 below.

TABLE 4

| Example | T-Peel | % Adhesive Transfer | 5° Shear |
|---|---|---|---|
| C9 | Split | | Split |
| C10 | Delaminated | | Delaminated |
| 11 | 207 | 18 | 11 |
| C12 | 150 | 4 | Split |
| 13 | 203 | 7 | 15 |
| 14 | 186 | 73 | 14 |
| C15 | 180 | 2 | 61 |
| C16 | 147 | 95 | 5 |
| C17 | 73 | 100 | 7 |

The non- or low-oil-containing porous polypropylene laminates, Examples C9, C10 and C12, showed adhesive failure to cotton. The non-porous control film laminates (C16 and C17) both showed essentially complete adhesive transfer to the cotton. The oil-containing porous film laminates generally showed good T-Peel values with relatively low levels of adhesive transfer to the cotton.

Examples 18–21

Laminates were prepared as described above for Example 4 except the adhesive coating weight (in grains/24 in²) was varied as indicated in Table 5. Example 21 was laminated at 150° F. (65° C.).

TABLE 5

| Example | Coating Weight | 24 Hour Peel | 168 Hour Peel |
|---|---|---|---|
| 18 | 2.8 | 13 | 10 |
| 19 | 5.5 | 15 | 12 |
| 20 | 8.3 | 17 | 15 |
| 21 | 5.5 | 13 | 12 |

The coating weight and lamination temperature did not appear to significantly effect the 180° peel release values of the polypropylene liner from the adhesive laminate. All the adhesive in the examples cleanly transferred to the porous film.

The adhesive-coated, oil-filled, porous film was then tested for its adhesion properties to cotton, as described above for Examples 1-17. The results of this testing is set forth in Table 6.

TABLE 6

| Example | T-Peel | % Adhesive Transfer | 5° Shear |
| --- | --- | --- | --- |
| 18 | 77 | 0 | 15 |
| 19 | 287 | 37 | 14 |
| 20 | 313 | 77 | 23 |
| 21 | 266 | 13 | 17 |

The results in Table 6 show that by increasing coating weight the peel adhesion can be increased, however, also increasing the amount of adhesive transfer. Lamination temperature appeared to have no significant effect on subsequent peel to cotton, but appeared to reduce adhesive transfer.

Example 22

A laminate was prepared in accordance with Example 4 except the liner had a matte surface (Ra=56) in contact with the adhesive layer as compared to a smooth surface. The 180° peel release values for this liner were 275, 147 and 130 (grams/in width) at 4, 24 and 168 hours, respectively. The matte film as such was less functional as a release liner in the laminate construction.

Example 23

A laminate was prepared in accordance with Example 5 with the exception that the adhesive was a tackified Kraton TM 1107 (styrene-isoprene-styrene block copolymer available from Shell Chemical Co.). The adhesive was coated at 5.5 grams/24 in$^2$ and dried in air for 1 minute then at 150° F. (68° C.) for 5 minutes. The 180° peel release value for the liner was 500 gm/in width at 24 hours and 318 grams/in width at 168 hours. The adhesion of the adhesive on porous film was then tested for its adhesion to cotton after 168 hours as per Examples 1-21, however, the adhesive would not adhere to the cotton substrate.

Example 24

A laminate was prepared in accordance with Examples 1-8 using a polyester liner film (Scotchpar TM LS, 2.4 mil thick, Ra=3, containing an SiO$_2$ slip agent available from 3M Company, St. Paul, Minn). The adhesive-coated liner (4.0 grains/24in$^2$ coating weight) was then laminated to the oil-filled porous film of Examples 1-8 at room temperature. The laminate was then tested at 24 hours and 168 hours for release values of the PET film. The PET was removed at 180° at peel values of 31 grams/in and 33 grams/in at 24 and 168 hours, respectively, indicating that laminate construction. The adhesive-coated porous film was then T-peel and 5° static shear tested against cotton, as described in Examples 1-8. The T-peel value was 250 grams/in width and the static shear was 15 minutes/in$^2$. Adhesive transfer to cotton was about 10%.

Example 25

A laminate was prepared as described above for Example 24 except that the liner was a PET film (Scotchpar TM HC, 4.0 mil thick) without slip agent. The 180 degree peel release values for this liner were 25 and 30 grams/in width at 24 and 168 hours, respectively. The T-peel and 5° static shear to cotton were 200 grams/in width and 5 minutes, respectively, for the adhesive-coated porous film. Adhesive transfer was about 8 percent. This was a functional laminate construction.

Examples 26 and 27

Laminates were prepared in accordance with Example 24 using a bilayer film liner having slip agent (SiO$_2$) in one layer. The Example 26 laminate was produced with the adhesive coated on the side of the liner with slip agent, and the Example 27 laminate was produced with the adhesive coated on the layer of the liner without slip agent (PET Scotchpar TM HP, 2.0 mil thick). The two laminates were tested for 180 degree peel release, with the resulting adhesive-coated porous film tested against cotton as described above. The results are given in Table 7 below.

TABLE 7

| Example | 180° Peel 24 hours | 180° Peel 168 hours | T-peel Cotton | 5° Shear Cotton | Adhesive Transfer % |
| --- | --- | --- | --- | --- | --- |
| 26 | 20 | 21 | 160 | 9 | 7% |
| 27 | 27 | 27 | 153 | 9 | 7% |

The slip agent appeared to slightly lower the 180° release value for the liner in the Example 26 laminate, however, both sides of the film functioned as superior release liners.

Examples 28 and 29

Two laminates were prepared as described above for Example 24 using liners of a polypropylene/polyethylene copolymer (Fina 620H available from Fina Oil & Chemical Co.) and a different repulpable adhesive for Example 28. The Example 28 repulpable adhesive was placed into a solution of 170 parts ethyl acetate, 32 parts methanol and 10.3 parts water. The adhesive comprised 100 parts butyl acrylate/acrylic acid (75/25, with an inherent viscosity of from 1.2 to 1.4) with 84.3 parts of a phosphoric acid ester (Gafac TM PE-510, density is 1.08 to 1.09 and an acid number pH 5.5 of 49-59), 24.6 parts rosin (Foral TM AX a wood rosin comprised predominately of abietic acid) and 3.6 parts KOH, prepared substantially as described in U.S. patent Ser. No. 580,116. The solutions were coated onto the polyethylene/polypropylene copolymer liner film and dried. The performance results as described for the previous laminates are given in Table 8 below.

TABLE 8

| Example | 180° Peel/ 24 hours | 180° Peel/ 168 hours | T-peel Cotton | 5° Shear Cotton | Adhesive Transfer % |
| --- | --- | --- | --- | --- | --- |
| 28 | 8 | 10 | 243 | 32 | 0 |
| 29 | 28 | 37 | 93 | 21 | 10 |

The adhesive of Example 28 provided superior 180° peel release values for the liner and good adhesion performance to cotton.

Cotton T-peel Test

The cotton material was cut into strips 2 inches by 5 inches. The adhesive-coated porous film was then placed on the cotton strip and rolled down, with a 4.5 pound roller. The cotton layer was then placed in one jaw of an Instron TM tensile tester with the porous film placed in the opposing jaw. The jaws were operated at a crosshead speed of 12 inches/minute with a 1 inch wide adhesive on the porous film. The peel was about 4 to 5 inches depending on the sample size. The test was performed at room temperature at times after 168 hours from lamination.

5 Degree Static Shear to Cotton

The cotton material was cut into strips 2 inches by 3 inches. The cotton strips were then attached to a 3 inch by 3 inch metal panel using double-coated tape (Scotch TM 401) on an adjustable shear stand. A one inch length of the adhesive-coated porous film was then attached to the cotton with a 4.5 pound rolldown. A 200 gram weight was hung from the porous film, and the amount of time required for failure was recorded. The adhesive was 1 inch (2.54 cm) wide. The tests were run at the same time as the cotton T-peel test.

Other embodiments of the invention will be apparent to those skilled in the art from the consideration of the specification or practice of the invention disclosed herein. It is intended that the specifications and examples be considered as exemplary, with the true scope and spirit of the invention being indicated by the following claims.

We claim:

1. A laminate comprising an oil or oil-like additive containing porous substrate, an acrylate pressure-sensitive adhesive layer, and an overlying thermoplastic film release liner having a first face without any release coating, said first face having said acrylate pressure-sensitive adhesive thereon such that the film release liner can be removed from said pressure-sensitive adhesive at a 180° peel release value of less than 100 g/in width wherein the laminate is formed by process of laminating said release liner having said acrylate pressure-sensitive adhesive to said oil-containing substrate.

2. The laminate of claim 1 wherein the oil or oil-like additive containing porous substrate comprises a microporous film of a crystallizable continuous polymeric matrix with a separate oil-containing phase comprising a mineral oil, glycerin, petroleum jelly, polyethylene, polytetramethylene oxide or soft carbowax.

3. The laminate of claim 2 wherein the separate oil-containing phase comprises a mineral oil.

4. The laminate of claim 3 wherein the acrylate pressure-sensitive adhesive comprises a repulpable acrylate adhesive.

5. The laminate of claim 4 wherein the repulpable acrylate adhesive comprises an at least partially neutralized acrylic acid ester of a non-tertiary alkyl alcohol polymerized with a vinyl carboxylic acid monomer with a water-dispersable tackifier and plasticizer.

6. The laminate of claim 5 wherein the copolymer comprises 60–85 weight percent of the acrylic acid ester and 40–25 weight percent vinyl carboxylic acid neutralized with a base to form salts of at least a portion of the carboxylic acid moieties.

7. The laminate of claim 6 wherein the thermoplastic release liner is a polyolefin film having a 180° peel release value of less than 50 gm/in width in the laminate.

8. The laminate of claim 6 wherein the thermoplastic release liner is a polyester film having a 180° peel release value of less than 50 gm/in width in the laminate.

9. The laminate of claim 1 wherein the adhesive layer is a continuous layer.

10. The laminate of claim 2 wherein the adhesive layer is an intermittent coating.

11. The laminate of claim 4 wherein the thermoplastic release liner first face has an Ra value of less than 40.

12. The laminate of claim 11 wherein the thermoplastic release liner first face has an Ra value of less than 20.

13. The laminate of claim 4 wherein the oil or oil-like additive containing porous substrate is a microporous film having at least 5% of the oil-containing phase.

14. The laminate of claim 4 wherein the oil or oil-like additive containing porous substrate is a microporous film having at least 20% of the oil-containing phase.

* * * * *

UNITED STATES PATENT AND TRADEMARK OFFICE
CERTIFICATE OF CORRECTION

PATENT NO. : 5,242,726
DATED : September 7, 1993
INVENTOR(S) : Pariseau et al.

It is certified that error appears in the above-identified patent and that said Letters Patent is hereby corrected as shown below:

Column 7, line 54, after the word "that" and before the word "laminate", insert --PET functioned as an excellent release liner in the--.

Signed and Sealed this

Twenty-ninth Day of March, 1994

Attest:

BRUCE LEHMAN

Attesting Officer    Commissioner of Patents and Trademarks